US00PP13876P29

(12) United States Plant Patent
Kelaidis

(10) Patent No.: US PP13,876 P2
(45) Date of Patent: Jun. 10, 2003

(54) DELOSPERMA PLANT NAMED 'KELAIDIS'

(76) Inventor: Panayoti Kelaidis, 7530 E. Mississippi Dr., Denver, CO (US) 80231

( * ) Notice: Subject to any disclaimer, the term of this patent is extended or adjusted under 35 U.S.C. 154(b) by 0 days.

(21) Appl. No.: 10/080,604

(22) Filed: Feb. 22, 2002

(51) Int. Cl.[7] ..... A01H 5/00

(52) U.S. Cl. ..... Plt./263

(58) Field of Search ..... Plt./263

(56) References Cited

PUBLICATIONS http://www.hotpix.com/pc1414.htm.*
http://www.csu.org/cgi–bin/xeri/Xeriinclude?Xeridetail?PIS–dc.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Delosperma plant named 'Kelaidis', characterized by its compact, prostrate and spreading plant habit; freely branching growth habit, dense and bushy growth habit; light pink-colored flowers; and excellent garden performance.

2 Drawing Sheets

BOTANICAL CLASSIFICATION/CULTIVAR DESIGNATION

*Delosperma cooperi* cultivar Kelaidis.

BACKGROUND OF THE INVENTION

The present Invention relates to a new and distinct cultivar of Delosperma plant, botanically known as *Delosperma cooperi*, and hereinafter referred to by the name 'Kelaidis'.

The new Delosperma was discovered and selected by the Inventor in a controlled environment in Denver, Colo. in 1998 as a naturally-occurring whole plant mutation of an unidentified selection of *Delosperma cooperi,* not patented.

Asexual reproduction of the new cultivar by cuttings taken in a controlled environment in Denver, Colo. since 1998, has shown that the unique features of this new Delosperma are stable and reproduced true to type in successive generations.

SUMMARY OF THE INVENTION

Plants of the cultivar Kelaidis have not been observed under all possible environmental conditions. The phenotype may vary somewhat with variations in environment and culture such as temperature without, however, any variance in genotype.

The following traits have been repeatedly observed and are determined to be the unique characteristics of 'Kelaidis' . These characteristics in combination distinguish 'Kelaidis' as a new and distinct cultivar:

1. Compact, prostrate and spreading plant habit.
2. Freely branching growth habit, dense and bushy growth habit.
3. Light pink-colored flowers.
4. Excellent garden performance.

Plants of the new Delosperma are most similar to plants of the parent, the unidentified selection of *Delosperma cooperi*, however plants of the new Delosperma differ from plants of the parent selection primarily in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Delosperma.

The photograph on the first sheet comprises a side perspective view of a typical plant of 'Kelaidis'.

The photograph on the second sheet is a close-up view of a typical flower and leaves of 'Kelaidis'.

DETAILED BOTANICAL DESCRIPTION

Plants used for the aforementioned photographs and following observations and measurements were planted into one-gallon containers and grown for about four months in a polyethylene-covered greenhouse in Denver, Colo. During the production of the plants, the day temperatures ranged from 13 to 27° C. and night temperatures ranged from 4 to 18° C. In the following description, color references are made to The Royal Horticultural Society Colour Chart, 1995 Edition, except where general terms of ordinary dictionary significance are used.

Botanical classification: *Delosperma cooperi* cultivar Kelaidis.

Parentage:

Naturally-occurring whole plant mutation of an unidentified selection of *Delosperma cooperi,* not patented.

Propagation:

*Type.*—By cuttings.

*Time to initiate roots.*—Summer: About 10 days at 22° C. Winter: About 14 days at 22° C.

*Time to produce a rooted young plant.*—Summer: About 42 days at 21° C. Winter: About 48 days at 21° C.

*Root description.*—Fine, freely branching.

Plant description

*Form.*—Compact, prostrate and spreading plant habit. Freely branching growth habit with branching at potentially every node, dense and bushy appearance. Leaves, succulent.

*Plant height.*—About 4.5 cm.

*Plant diameter.*—About 23 cm.

*Foliage description.*—Arrangement: Opposite, simple; crowded. Length: About 1 cm. Width: About 2 mm. Shape: Linear; nearly cylindrical. Apex: Acute. Base: Decurrent. Margin: Entire. Orientation: Recurved. Texture, upper and lower surfaces: Glabrous; succulent. Venation pattern: Parallel. Color: Young and fully expanded foliage, upper surface: Darker than 144A. Young and fully expanded foliage, lower surface: Darker than 144A. Venation, upper and lower surfaces: Darker than 144A.

Flower description:

*Flower type and habit.*—Single rotate flowers; typically one flower per terminal.

*Natural flowering season.*—Plants flower continuously year round.

*Flower longevity on the plant.*—About two to three days.

*Fragrance.*—None detected.

*Flowers.*—Diameter: About 3.8 cm. Depth: About 1.6 cm.

*Flower buds.*—Length: About 7 mm. Diameter: About 5 mm. Shape: Oblong. Color: Close to 8C.

*Petals.*—Quantity/arrangement: About 32 arranged in a single row. Length: About 1.9 cm. Width: About 1.5 mm. Orientation: About 70° from vertical. Aspect: Straight, flat. Shape: Linear. Apex: Acute or emarginate. Base: Attenuate. Margin: Entire. Texture, upper and lower surfaces: Smooth, waxy. Color: When opening, upper surface: Close to 8C faintly overlain with close to 52B. When opening, lower surface: Close to 8C faintly underlain with close to 52B. Fully opened, upper surface: Close to 8C overlain with close to 52B; color becoming closer to 52A with development. Fully opened, lower surface: Close to 8C underlain with close to 52B.

*Sepals.*—Quantity/arrangement: About five fused into a cupped shape calyx. Length: About 8 mm. Diameter: About 3 mm. Shape: Deltoid, elongated. Apex: Acute. Base: Fused. Margin: Entire. Texture, upper and lower surfaces: Papillate; succulent. Color, upper and lower surfaces: 144A.

*Peduncles.*—Length: About 1.1 cm. Diameter: About 2.5 mm. Strength: Strong, flexible. Angle: Erect. Texture: Papillate. Color: 144A.

*Reproductive organs.*—Stamens: Quantity per flower: About 50. Filament length: About 3 mm. Filament color: Close to 154A. Anther shape: Oblong. Anther length: Less than 1 mm. Anther color: Close to 155D. Pollen amount: Abundant. Pollen color: Close to 6A to 9A. Pistils: Quantity per flower: About 15. Style length: About 3.5 mm. Style color: Close to 4D. Stigma shape: Acute. Stigma color: Close to 4D. Ovary color:. Close to 154A.

*Seed/fruit.*—Seed nor fruit production has not been observed.

Disease/pest resistance: Plants of the new Delosperma have not been noted to be resistant to pathogens or pests common to Delosperma.

Weather tolerance: Plants of the new Delosperma have been observed to be tolerant to rain, wind and temperatures ranging from 0 to at least 38° C.

It is claimed:

1. A new and distinct cultivar of Delosperma plant named 'Kelaidis', as illustrated and described.

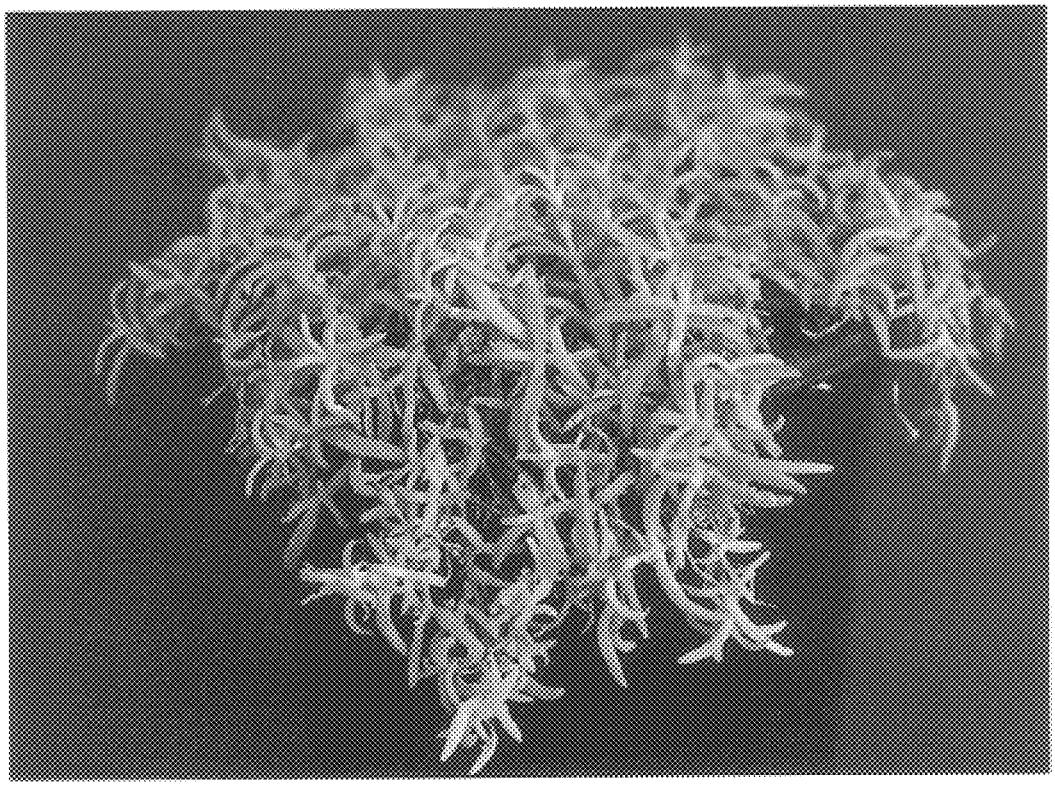

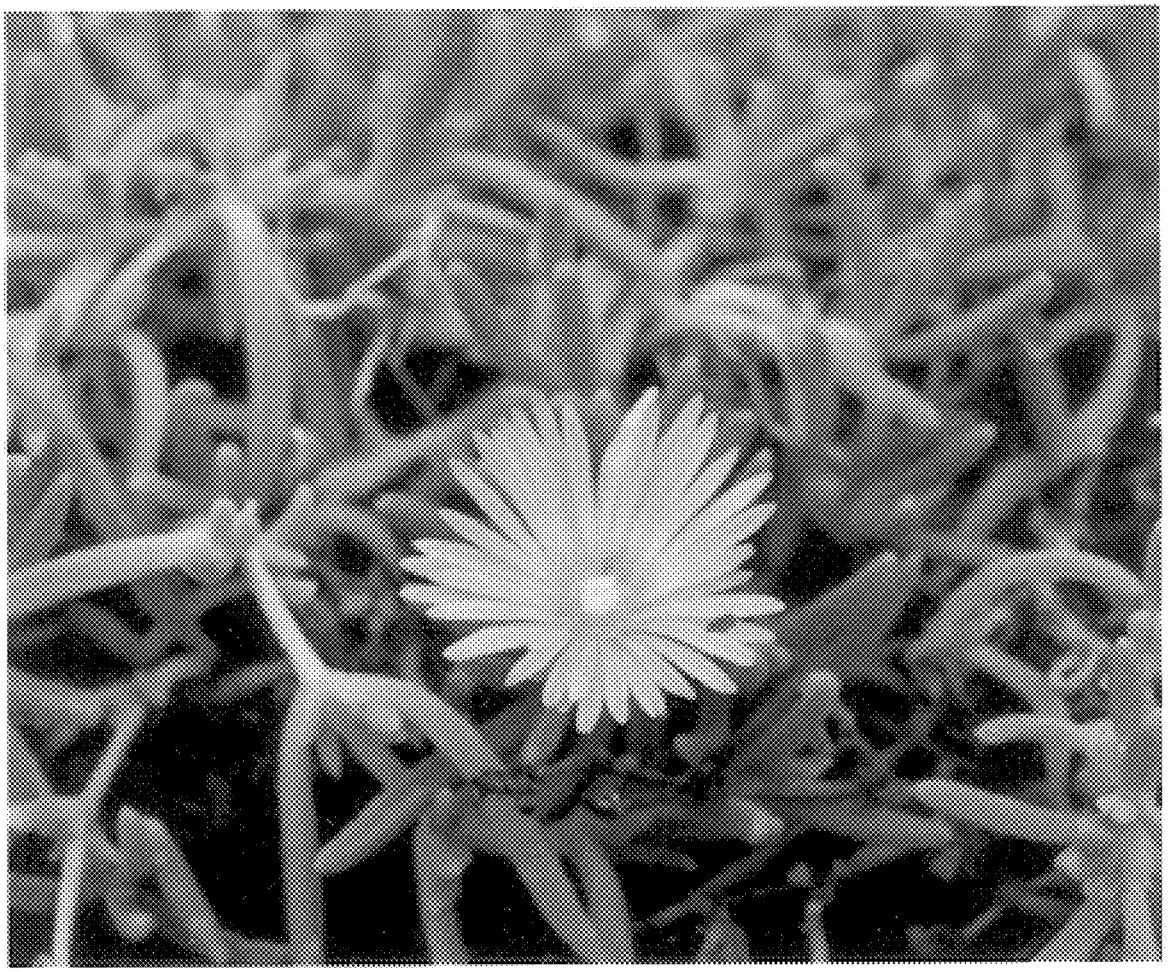

* * * * *